(12) United States Patent
Adams et al.

(10) Patent No.: US 6,620,965 B1
(45) Date of Patent: Sep. 16, 2003

(54) PROCESS FOR VINYL ACETATE

(75) Inventors: John R. Adams, Houston, TX (US); Willibrord A. Groten, Houston, TX (US); Speros P. Nemphos, League City, TX (US)

(73) Assignee: Catalytic Distillation Technologies

( * ) Notice: Subject to any disclaimer, the term of this patent is extended or adjusted under 35 U.S.C. 154(b) by 11 days.

(21) Appl. No.: 10/093,708

(22) Filed: Mar. 8, 2002

(51) Int. Cl.$^7$ .............................................. C07C 67/055

(52) U.S. Cl. ...................................... 560/245; 560/243

(58) Field of Search ................................. 560/243, 245

(56) References Cited

U.S. PATENT DOCUMENTS

| | | | |
|---|---|---|---|
| 3,404,177 A | * | 10/1968 | Baba |
| 3,840,590 A | * | 10/1974 | Fisher |
| 5,332,710 A | | 7/1994 | Nicolau et al. ............. 502/243 |
| 5,347,046 A | | 9/1994 | White et al. ................ 560/245 |
| 5,550,281 A | | 8/1996 | Cirjak et al. ................ 560/245 |
| 5,719,315 A | | 2/1998 | Tustin et al. ................ 560/238 |
| 5,990,344 A | | 11/1999 | Couves et al. .............. 560/245 |
| 6,225,496 B1 | * | 5/2001 | Baker |

* cited by examiner

Primary Examiner—Michael L. Shippen
(74) Attorney, Agent, or Firm—Kenneth H. Johnson

(57) ABSTRACT

A process for producing vinyl acetate comprising reacting ethylene, acetic acid and oxygen together in at least partially liquid phase in the presence of a catalyst comprising a noble metal component.

6 Claims, 1 Drawing Sheet

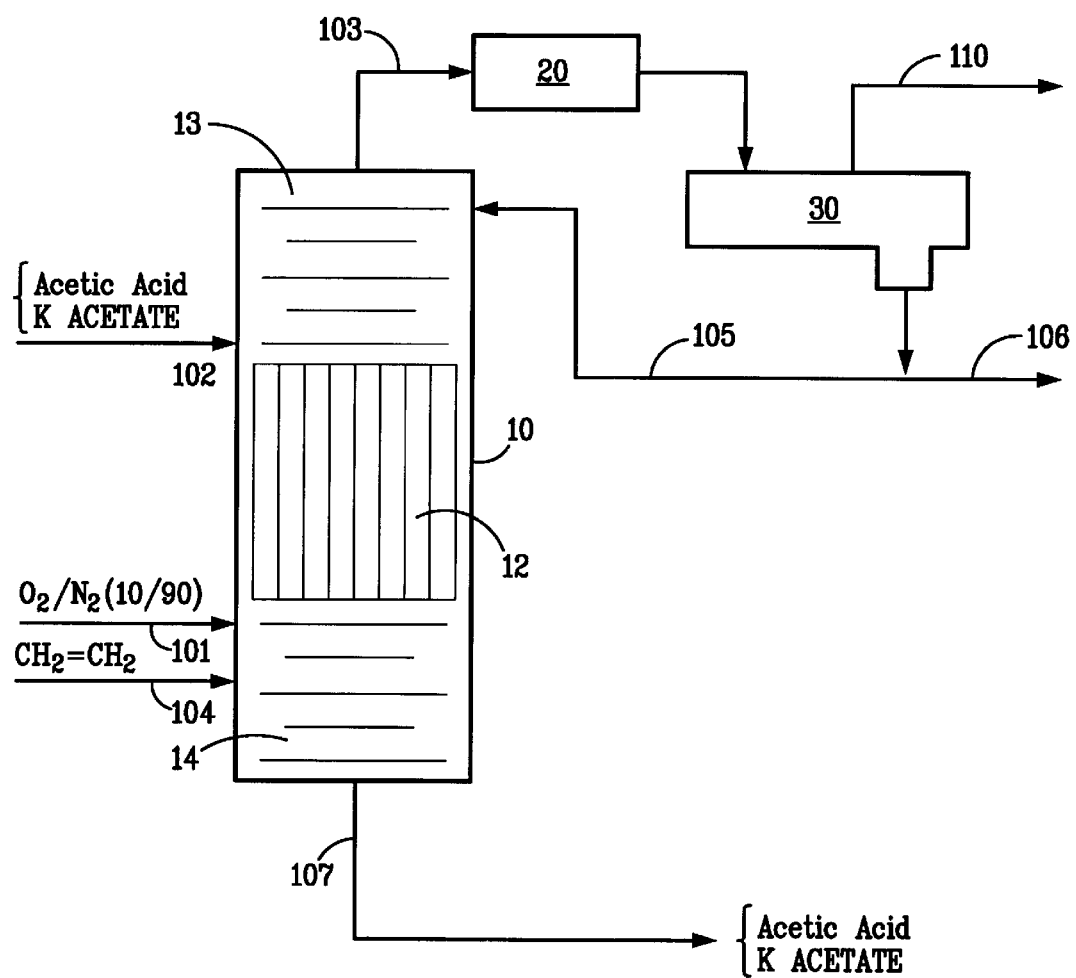

PROCESS FOR VINYL ACETATE

BACKGROUND OF THE INVENTION

FIELD OF THE INVENTION

The present invention relates to a process for oxyacylation of olefins or diolefins. In particular, the present invention is directed to a process for the production of vinyl acetate from ethylene, acetic acid and an oxygen-containing gas in the presence of a catalyst. More particular, the present invention is directed to a process for the production of vinyl acetate wherein both a liquid and vapor phase are present. Related Information Both liquid and gas phase reaction are known for the reaction. The basic chemical reaction is:

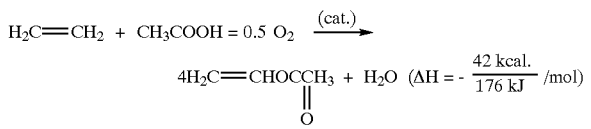

The liquid type usually requires a chloride salt while the gas type is chlorine free. The operational conditions for both processes are similar. In the liquid phase process, in the presence of palladium salts and redox systems, vinyl acetate and acetaldehyde are formed side by side. However, in the gas-phase process using palladium or chlorine-free palladium salts, vinyl acetate is almost exclusively formed. Furthermore, no noticeable corrosion problems arise with the gas-phase process.

Some liquid processes use a supported palladium acetate catalyst. The metal and salt catalysts contain alkali acetates and other components which serve to increase activity and selectivity. During the course of the reaction, the catalyst goes through a change, especially in relation to its alkali acetate content. The alkali acetates migrate from the catalyst as a consequence of the reaction conditions and must therefore be constantly renewed. The vapor-phase process differs from the liquid in that very little acetaldehyde forms. A gaseous mixture of acetic acid, ethylene, and oxygen is blown over the catalyst in a tubular reactor and the exit stream, containing vinyl acetate, unreacted starting materials, water, and small amounts of acetaldehyde, carbon dioxide, and other by-products, is separated by a combination of scrubbers and distillation stages.

The commercial production of vinyl acetate by reacting ethylene, acetic acid and oxygen together in the gas phase in the presence of a fixed bed catalyst containing palladium, a promoter metal, and an alkali metal acetate is known. Usually the fixed bed catalyst components are supported on a porous carrier such as silica, zirconia or alumina. There are various patents such U.S. Pat. No. 3,759,839 and Great Britain Patent 1,266,623 which disclose the manufacture of vinyl acetate utilizing palladium promoted catalyst. In a typical vinyl acetate production process, ethylene, acetic acid and oxygen are introduced into a reactor via an inlet. The reactants are contacted with a palladium-containing catalyst and react to produce an outlet stream which is removed from the reactor and cooled. Vinyl acetate, water and the unreacted acetic acid in the outlet stream are condensed and separated for finer purification. The remaining gaseous components of the outlet stream (e.g., ethylene) are compressed and recycled.

Currently, the preferred route to vinyl acetate is the direct reaction of ethylene, acetic acid and oxygen to produce vinyl acetate, water and byproducts. The preferred version of this process uses a heterogeneous catalyst and is performed in the vapor phase at 2–5 bar at 300° F. Because of the explosion hazards associated with this reaction, the reaction must be performed with less than a stoichiometric amount of oxygen; hence, conversions of ethylene, acetic acid and oxygen are typically 10–15%, 15–30% and 60–90% respectively. About 5–10% of the ethylene is converted to carbon dioxide and about 1% is converted to acetaldehyde. The low ethylene and acetic acid conversions per pass require extensive recycling along with a carbon dioxide removal system. Although the capital costs of an ethylene-acetic acid-oxygen-based vinyl acetate plant are high, these capital costs are offset by the generally low costs of ethylene and acetic acid. Thus, a need exists for a process for preparing vinyl acetate having higher conversions per pass and lower yield loss to carbon dioxide than the ethylene-acetic acid-oxygen-based route. The process of the present invention, unlike the ethylene-acetic acid-oxygen-based route, indeed produces vinyl acetate in high conversions per pass and does not produce significant quantities of carbon dioxide.

Other attempts at producing vinyl acetate have also been tried. For example, a number of these attempts seek to prepare vinyl acetate from mixtures of carbon monoxide and hydrogen (synthesis gas) because of the very low cost of raw materials. As initial steps, these schemes convert synthesis gas to methanol or dimethyl ether. In addition, many combinations have been tried in which methyl acetate (produced from methanol and recycled acetic acid) or dimethyl ether are carbonylated to produce acetic anhydride. In some schemes, acetic anhydride is partially hydrogenated to produce EDA and acetic acid. In still other schemes, the methyl acetate or dimethyl ether is carbonylated in the presence of hydrogen to produce EDA and acetic acid in one step. Variations on this approach include reacting methanol or methyl acetate with hydrogen and carbon monoxide to produce acetaldehyde and water or acetaldehyde and acetic acid, respectively; however, the selectivity to acetaldehyde in these reactions is poor. The resulting acetaldehyde is then reacted with the acetic anhydride to produce EDA.

It is known to produce vinyl acetate by reaction of ethylene, oxygen and acetic acid using a catalyst comprising a palladium group metal and/or a compound thereof, gold and/or a compound thereof, and copper, nickel, cobalt, iron, manganese, lead or silver, or a compound thereof, preferably deposited on a support material. U.S. Pat. No. 5,332,710, U.S. Pat. No. 5,347,046 and U.S. Pat. No. 5,567,839, among others, disclose methods of producing catalysts of this type suitable for the present invention.

An advantage of the present mixed phase process is over the gas or liquid phase alone. Because of the presence of a liquid phase, the temperature in the reactor is better controlled by allowing a portion of the liquid to form more boil up.

SUMMARY OF THE INVENTION

The present invention is a process for producing vinyl acetate comprising reacting ethylene, acetic acid and oxygen together in at least partially liquid phase in the presence of a catalyst comprising a noble metal component by:

(A). concurrently passing said ethylene, acetic acid and oxygen together in concurrent flow through a reaction zone containing said catalyst to produce an effluent containing vinyl acetate under conditions of temperature and pressure such that the temperature of the effluent is above its boiling point and below its dew point, whereby at least a portion but less than all of the material in said reaction zone is in the vapor phase, preferably the flow is downflow or (B). a. feeding ethylene, acetic acid and oxygen to a reaction distillation zone;

b. concurrently in said reaction distillation zone:
  i. contacting ethylene, acetic acid and oxygen in the presence of said catalyst to produce a reaction mixture containing vinyl acetate and
  ii. fractionating said reaction mixture into an overheads containing vinyl acetate and a bottoms containing acetic acid and water, the catalyst may be prepared as distillation structure.

The reaction as conducted is strongly exothermic and is carried out suitably at 150–300° F. and 2–5 bar. The explosion limit determines the $O_2$ content in the feed mixture which results in ethylene conversion (approximately 10%) in conventional vapor or liquid-phase processes. Oxygen concentrations on the order of 10 to 20 vol.% or higher are contemplated for use in the present process.

BRIEF DESCRIPTION OF THE DRAWING

The FIGURE is a schematic representation of one embodiment of the present invention.

DETAILED DESCRIPTION

The temperature in the concurrent flow process is conveniently controlled by the pressure used. The temperature in the reactor and catalyst bed is limited to the boiling point of the effluent at the pressure applied, notwithstanding the magnitude of the exotherm. A small exotherm may cause only a few percent of the liquid in the reactor to vaporize whereas a large exotherm may cause 30–90% of the liquids to vaporize. The temperature, however, is not dependent on the amount of material vaporized but the composition of the material being vaporized at a given pressure. That "excess" heat of reaction merely causes a greater boil up (vaporization) of the material present. The present process operates with an outlet pressure lower than the inlet pressure.

Preferably the bed is vertical with the feed passing downward through the bed and exiting after reaction through the lower end of the reactor. The reactor may be said to run in a quasi-isothermal manner.

Once the reaction is initiated, an exotherm develops and must be controlled to prevent a runaway reaction. The low pressures disclosed herein have the very great advantage of lower capital cost and operating cost than traditional processes. The reaction product in the present invention is at a higher temperature than the feed into the reactor with a portion being vapor and a portion liquid. The reactor is operated at a high weight hourly space velocity (6–30 $hr^{-1}$ WHSV, preferably 10–30 $hr^{-1}$).

The oxygen may be present at any level, e.g., 1 vol.% that it is possible to operate the reaction up to the amount determined to be an explosive mixture with ethylene under the conditions of the reaction. The oxygen is usually fed with an inert gas such as nitrogen, but CO and $CO_2$ which are by-products of the reaction, may also be used.

The FIGURE illustrates one catalytic distillation embodiment of the present process. The oxyacylation catalyst 12 is situated in the mid section of column 10 with a stripping section 14 below and a rectification 13 above. The catalyst is prepared in form to serve as both a distillation structure and the catalyst for the reaction. Oxygen containing gas is fed through line 101 below the catalyst bed as is ethylene via line 104. Acetic acid and potassium acetate are fed above the catalyst via line 102. The conditions in the CD reactor are maintained to hold the acetic acid in the catalyst bed and to cause the oxygen and ethylene to rise into the bed, where the reaction occurs. The unreacted oxygen (and any inert gas in the oxygen feed) aid in stripping the vinyl acetate from the reaction mixture and are taken off as overheads via line 103 to condenser 20 and accumulator 30, where uncondensed materials (oxygen, nitrogen and ethylene) are removed through line 110. Vinyl acetate product is recovered via line 106 and a portion returned to the column as reflux via line 105. Water, unreacted acetic acid and potassium acetate are removed as bottoms 107.

The catalyst typically is in the form of extrudates having a diameter of 1/8, 1/16 or 1/32 inches and an L/D of 1.5 to 10 or other shapes, such as polylobs and spheres having the same diameters. The catalyst may be directly loaded into the concurrent flow reactor which includes supports and reactant distribution structures. However, in their regular form they form too compact a mass and may then be prepared in the form of a catalytic distillation structure for use in the catalytic distillation reaction. This structure may also be used in the concurrent flow reaction. The catalytic distillation structure must be able to function as catalyst and as mass transfer medium. The catalyst must be suitably supported and spaced within the column to act as a catalytic distillation structure. In a preferred embodiment the catalyst is contained in a woven wire mesh structure as disclosed in U.S. Pat. No. 5,266,546, which is hereby incorporated by reference. More preferably the catalyst is contained in a plurality of wire mesh tubes closed at either end and laid across a sheet of wire mesh fabric such as demister wire. The sheet and tubes are then rolled into a bale for loading into the distillation column reactor. This embodiment is described in U.S. Pat. No. 5,431,890 which is hereby incorporated by reference. Other catalytic distillation structures useful for this purpose are disclosed in U.S. Pat. Nos. 4,731,229, 5,073,236, 5,431,890 and 5,730,843 which are also incorporated by reference. The catalysts are those known in the art for this reaction as described in U.S. Pat. Nos. 5,854,171, 5,859,287, 5,990,344, 5,998,659, 6,072,078, 6,107,513, 6,107,514 and 6,114,571, which are incorporated herein in their entirety.

The operation of the distillation column reactor results in both a liquid and vapor phase within the distillation reaction zone. A considerable portion of the vapor is nitrogen while a portion is vaporous hydrocarbon. Actual separation may only be a secondary consideration.

Without limiting the scope of the invention it is proposed that the mechanism that produces the effectiveness of the present process is the condensation of a portion of the vapors in the reaction system, which occludes sufficient ethylene in the condensed liquid to obtain the requisite intimate contact between the ethylene and the acetic acid in the presence of the catalyst to result in their reaction.

The result of the operation of the process in the distillation column reactor is that higher oxygen concentration may be used without exceeding the explosive concentration. As in any distillation there is a temperature gradient within the distillation column reactor. The temperature at the lower end of the column contains higher boiling material and thus is at a higher temperature than the upper end of the column.

It is believed that in the present distillation column reaction, it is a benefit first, because the reaction is occurring concurrently with distillation, and the initial reaction products and other stream components are removed from the reaction zone as quickly as possible reducing the likelihood of side reactions. Second, because all the components are boiling the temperature of reaction is controlled by the boiling point of the mixture at the system pressure. The heat of reaction simply creates more boil up, but no increase in temperature at a given pressure. As a result, a great deal of control over the rate of reaction and distribution of products can be achieved by regulating the system pressure. A further benefit that this reaction may gain from distillation column reactions is the washing effect that the internal reflux provides to the catalyst thereby reducing polymer build up and coking.

Finally, the upward flowing oxygen feed acts as a stripping agent to help remove the vinyl acetate which is produced in the distillation reaction zone.

EXAMPLE

The experiments were carried out in a 1" diameter 20' long catalytic distillation column. The experiment (#30–46) involved ethylene gas and glacial acetic acid being fed to the column where in the presence of oxygen react to produce vinyl acetate. The acetic acid (containing 0.5% potassium acetate catalyst activator) was fed at the top of the catalyst bed while the ethylene and the oxygen (as a 10/90 $O_2/N_2$ Mix) were fed at the bottom of the column. The catalyst was a typical oxyacylation catalyst (e.g., Pd-Au/$SiO_2$, Pd 1–4.5%, Au 1–4.5%). Reaction conditions studied were in the 150–300° F. and 20–60 psig range.

The vinyl acetate product was drawn from the column as the overheads stream, while unreacted acetic acid (plus potassium acetate) and water byproduct were taken off as the bottom draw. Unreacted ethylene is vented to the flare along with nitrogen and the other gases.

The attached table presents some average results from two distinctly different sets of conditions. The results show producing vinyl acetate with good selectivity via the reactive distillation mode. The relatively low conversion rates (mass balance calculations based on oxygen conversions are in the order of 50%) are primarily the result of the low oxygen content gas employed (a 10/90 by vol. ratio of $O_2/N_2$). It was considered prudent to maintain the oxygen well below the reaction mixture explosion limits because of pilot equipment limitations. The excessive amounts of nitrogen flowing through the distillation column made stable refluxing difficult and allowed unreacted oxygen losses through the vent system.

TABLE

Vinyl Acetate CD Process
Run EDU 30–41

|  | Exp. #1 | Exp. #2 |
| --- | --- | --- |
| Conditions in Column |  |  |
| Pressure (psi) | 30 | 50 |
| Temperature (° F.) | 230 | 260 |
| Catalyst weight (lbs) | 0.75 | 0.75 |
| Inlet Feeds |  |  |
| Acetic Acid (lbs/hr) | 0.4 | 0.4 |
| (Contains 0.5% Potassium Acetate) |  |  |
| Ethylene (lbs/hr) | 0.3 | 0.3 |
| Oxygen/Nitrogen Mix (scfh) | 9.0 | 15.0 |
| Oxygen (lbs/hr) | 0.006 | 1.0 |
| Nitrogen (lbs/hr) | 0.6.0 | 1.0 |

TABLE-continued

Vinyl Acetate CD Process
Run EDU 30–41

|  | Exp. #1 | Exp. #2 |
| --- | --- | --- |
| Product Streams |  |  |
| Bottoms (lbs/hr) | 0.1 | 0.1 |
| Overheads (lbs/hr) | 0.3 | 0.3 |
| Vent (lbs/hr) | 1.0 | 1.5 |
| Product Streams (Analyses) |  |  |
| Bottoms (lbs/hr) |  |  |
| Acetic Acid | 0.0975 | 0.0975 |
| Water | 0.0015 | 0.0015 |
| Vinyl Acetate | 0.0009 | 0.0009 |
| Acetic Anhydride | Trace | Trace |
| Overheads (lbs/hr) |  |  |
| Vinyl Acetate | 0.009 | 0.024 |
| Water | 0.003 | 0.01 |
| Acetic Acid | 0.29 | 0.27 |
| Vent (lbs/hr) |  |  |
| Ethylene | 0.23 | 0.23 |
| $CO_2$ | 0.0013 | 0.0018 |
| Nitrogen | 0.72 | 1.2 |
| CO | 0.055 | 0.055 |

The invention claimed is:

1. A process for producing vinyl acetate comprising reacting ethylene, acetic acid and oxygen together in at least partially liquid phase in the presence of a catalyst comprising a noble metal component by:
   (A). concurrently passing said ethylene, acetic acid and oxygen together in concurrent flow through a reaction zone containing said catalyst to produce an effluent containing vinyl acetate under conditions of temperature and pressure such that the temperature of the effluent is above its boiling point and below its dew point, whereby at least a portion but less than all of the material in said reaction zone is in the vapor phase or
   (B). a. feeding ethylene, acetic acid and oxygen to a reaction distillation zone;
   b. concurrently in said reaction distillation zone:
      i. contacting ethylene, acetic acid and oxygen in the presence of said catalyst to produce a reaction mixture containing vinyl acetate and
      ii. fractionating said reaction mixture into an overheads containing vinyl acetate and a bottoms containing acetic acid and water.

2. The process according to claim 1 comprising reacting ethylene, acetic acid and oxygen together in at least partially liquid phase in the presence of a catalyst comprising a noble metal component by concurrently passing said ethylene, acetic acid and oxygen together in concurrent flow through a reaction zone containing said catalyst to produce an effluent containing vinyl acetate under conditions of temperature and pressure such that the temperature of the effluent is above its boiling point and below its dew point, whereby at least a portion but less than all of the material in said reaction zone is in the vapor phase.

3. The process according to claim 2 wherein the flow is downflow.

4. The process according to claim 1 comprising reacting ethylene, acetic acid and oxygen together in at least partially liquid phase in the presence of a catalyst comprising a noble metal component by:
   a. feeding ethylene, acetic acid and oxygen to a reaction distillation zone;

b. concurrently in said reaction distillation zone:
   i. contacting ethylene, acetic acid and oxygen in the presence of said catalyst to produce a reaction mixture containing vinyl acetate and
   ii. fractionating said reaction mixture into an overheads containing vinyl acetate and a bottoms containing acetic acid and water.

5. The process according to claim 4 wherein the catalyst comprises a distillation structure.

6. The process according to claim 1 wherein oxygen concentrations of 10 to 20 vol.% or higher are fed to the reaction.

* * * * *